United States Patent
Hasegawa

Patent Number: 6,115,450
Date of Patent: Sep. 5, 2000

[54] X-RAY FLUORESCENCE ANALYZER CAPABLE OF DETERMINING THE CENTER OF A SAMPLE

[75] Inventor: Kiyoshi Hasegawa, Chiba, Japan

[73] Assignee: Seiko Instruments Inc., Japan

[21] Appl. No.: 09/057,422

[22] Filed: Apr. 8, 1998

[30] Foreign Application Priority Data

Apr. 8, 1997 [JP] Japan .................................. 9-089472
Mar. 20, 1998 [JP] Japan .................................. 10-072790

[51] Int. Cl.$^7$ .................................. G01N 23/223
[52] U.S. Cl. .................................. 378/50; 378/44
[58] Field of Search .................................. 378/44, 50

[56] References Cited

U.S. PATENT DOCUMENTS 5,425,066  6/1995  Takahashi et al. .................. 378/50

FOREIGN PATENT DOCUMENTS 59-155704  9/1984  Japan .
62-148803  7/1987  Japan .
63-21844   1/1988  Japan .
6273146    9/1994  Japan .

Primary Examiner—David P. Porta
Assistant Examiner—Drew A. Dunn
Attorney, Agent, or Firm—Adams & Wilks

[57] ABSTRACT

An x-ray fluorescence analyzer which accomplishes determination of the center of a circular sample in an xy-plance, in which the sample is placed, by performing a first step of determining a provisional center, a second step of carrying out measurements by scanning in the x-axis direction, a third step of calculating the center of the sample in the x-axis direction, a fourth step of carrying out measurements by scanning in the y-axis direction, a fifth step of calculating the center of the sample in the y-axis direction, and a sixth step of determining coordinates of the center of the sample.

6 Claims, 6 Drawing Sheets

X-RAY FLUORESCENCE ANALYZER CAPABLE OF DETERMINING THE CENTER OF A SAMPLE

BACKGROUND OF THE INVENTION

The present invention relates to X-ray fluorescence analyzers.

In a system configuration shown in FIG. 9 a system controller 28, under control of an operating section 29, is controlled by, an operator to conventionally set each measuring point by moving a sample table 24 loaded with a sample by aligning crisscross lines on a sample observation monitor 27 with a desired part of the sample. When the sample to be measured is extremely small, an optical observation system such as a mirror 25, a receiver 26 and a display unit 27 having low magnifying power is usually used to observe a large area. This would, however, make it difficult to accomplish alignment on a sample monitor. One approach to this problem has been to employ an observation system switchable to a high magnification optical system. An alternative approach has been to measure the sample by using a scanning technique in which the sample is scanned in a lattice pattern with scanning intervals that are sufficiently narrow with respect to the dimensions of the sample, an operator determines the center of the sample from resultant two-dimensional profiles, and adopts measurement results obtained from that position.

It has been possible to achieve practically sufficient positioning by using the conventional sample monitor when samples were relatively large.

With the miniaturization of electronic components in recent years, however, it has become difficult to achieve their precise position alignment by a positioning technique using images presented on the sample monitor, due to the limits of image resolution and accuracy problems involved in aligning a target point for X-ray exposure with the crisscross lines on the sample monitor. In addition, there has been an increasing need for a precision positioning function because of significantly reduced positioning tolerances which would be required when a sample has been accidentally displaced as a result of a movement of a sample table in such a case where automatic measurements are to be performed after registering each measuring point of the sample.

On the other hand, the approach involving the switching to a high magnification optical system when it is difficult to align with the center of a sample with a low magnification optical system has a problem in that the system becomes too expensive, while the approach in which the center of the sample is determined from two-dimensional profiles has a problem in that it requires a considerable time, rendering these approaches impractical.

Accordingly, it is an object of the invention to provide means for enabling precise positioning of measuring points in a short time without using image information to overcome the aforementioned problems of the prior art.

SUMMARY OF THE INVENTION

To provide a solution to the aforementioned problems, the center of a circular sample, which is placed on the sample table and permits detection of X-ray fluorescence, is determined by performing a process including a first step in which the center of the circular sample is aligned with a spot exposed to X-ray radiation by using a sample monitor section to thereby determine a provisional center of the circular sample, a second step in which fluorescent X-ray intensities of individual points are obtained by using the provisional center as a reference under such conditions that the scanning range in the x-axis direction is set to twice the diameter of the circular sample and the interval between successive scanning points is made equal to the width of each spot exposed to an X-ray beam as measured in the x-axis direction, a third step in which the central x-coordinate of the sample is determined by calculating a center of gravity of the fluorescent X-ray intensities in the x-axis direction from the fluorescent X-ray intensities and x-coordinates obtained from the measurements in the x-axis direction, a fourth step in which fluorescent X-ray intensities of individual points are obtained by using the central x-coordinate of the sample and the y-coordinate of the provisional center as a reference under such conditions that the scanning range in the y-axis direction is set to twice the diameter of the circular sample and the interval between successive scanning points is made equal to the width of each spot exposed to the X-ray beam as measured in the x-axis direction, and a fifth step in which the center of the sample in the y-axis direction is determined by calculating the y-coordinate of a center of gravity of the fluorescent X-ray intensities from the fluorescent X-ray intensities and y-coordinates obtained from the measurements in the y-axis direction.

The expression center of gravity as used in this Specification is defined as follows.

Provided that the fluorescent X-ray intensity at an i-th scanning point is $I_i$ and the x-coordinate of the i-th scanning point is $x_i$, for example, the center of gravity in the x-axis direction is expressed as follow:

Center of gravity in x-axis direction=$\Sigma(I_i*x_i)/\Sigma I_i$

If i=3, for example, the center of gravity in the x-axis direction is represented by the expression $(I_1*x_1+I_2*x_2+I_3*x_3)/(I_1+I_2+I_3)$.

[Operational Features]

Operation of the invention is described with reference to FIG. 8.

First, a provisional center 16 of a circular sample 15 is determined. Second, measurements are performed by scanning in the x-axis direction using the provisional center as a reference point and a fluorescent X-ray intensity distribution 20 in the x-axis direction is obtained. Third, coordinates 18 are obtained by calculating a center of gravity from the fluorescent X-ray intensity distribution 20 in the x-axis direction and x-coordinates of individual scanning points. When the interval between successive measuring points by scanning is reduced, the coordinates 18 can be regarded as those of the central point of a line segment 19. Fourth, measurements are performed by scanning in the y-axis direction using the x-coordinate of the coordinates 18 and the y-coordinate of the provisional center as a reference point and a fluorescent X-ray intensity distribution 21 in the y-axis direction is obtained. Fifth, coordinates 17 are obtained by calculating a center of gravity from the fluorescent X-ray intensity distribution 21 in the y-axis direction and y-coordinates of individual scanning points by regarding the central coordinates as the central point of a line segment 14, whereby the center of the circular sample is obtained.

DETAILED DESCRIPTION OF THE INVENTION

Figure 1:
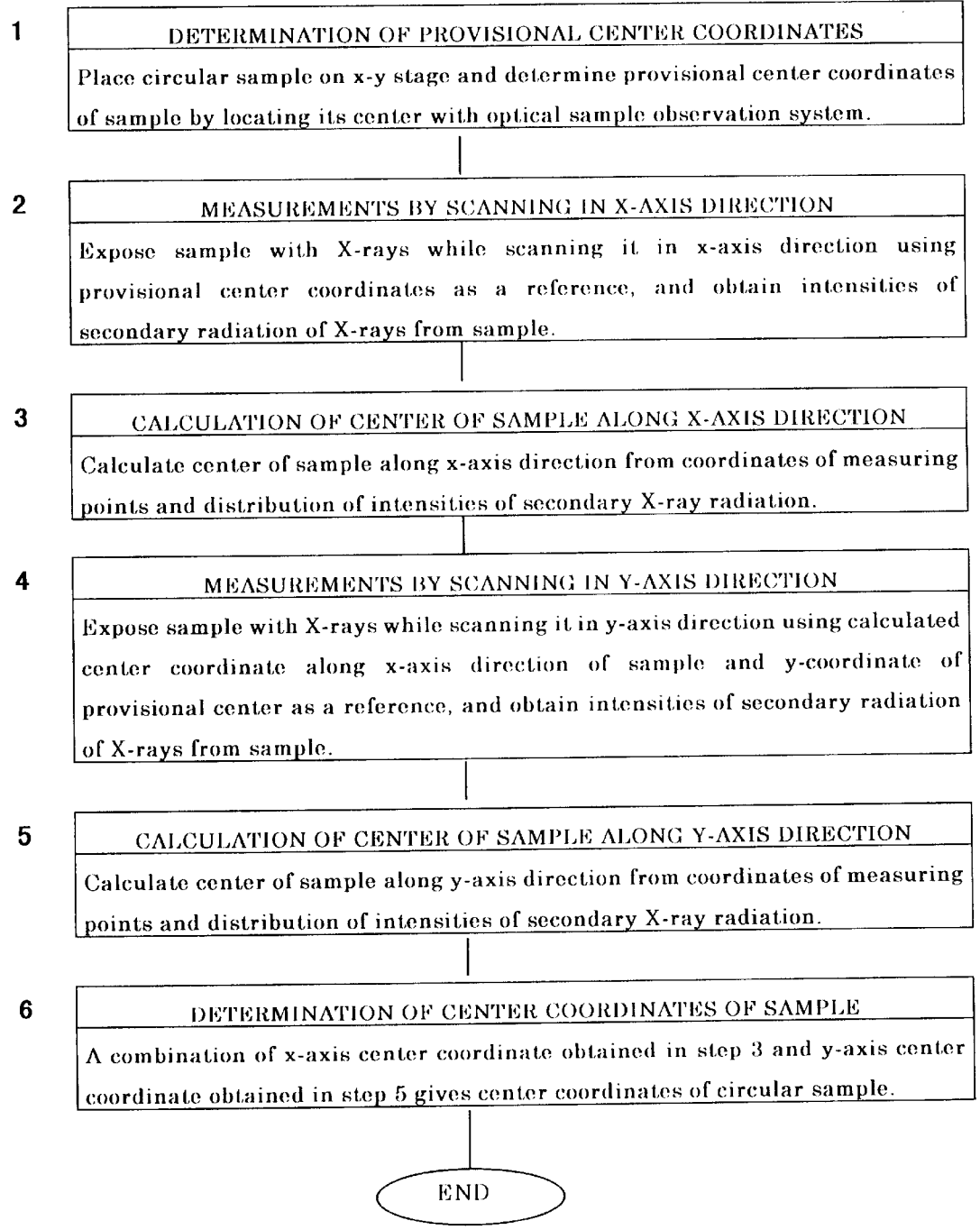
FIG. 1 is a flowchart presenting a procedure which is followed in determining the center of a circular sample.
Figure 2:
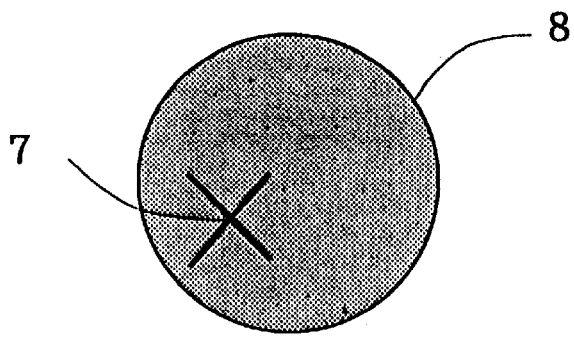
FIG. 2 is a diagram illustrating a relationship between a provisional center and the circular sample.
Figure 3:
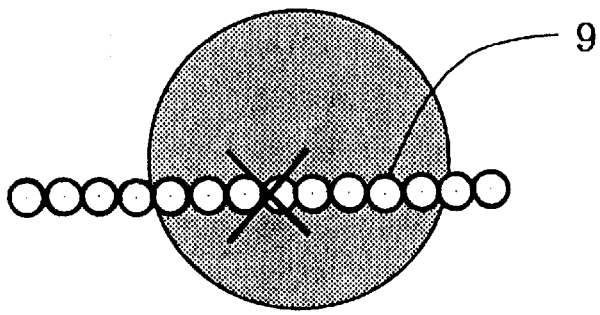
FIG. 3 is a diagram illustrating measurements performed by scanning in the x-axis direction.
Figure 4:
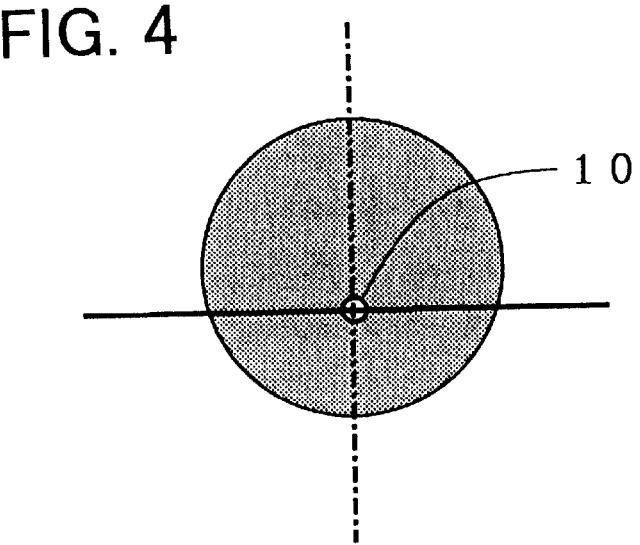
FIG. 4 is a diagram illustrating a process in which the x-coordinate of the center of the circular sample is determined based on a center of gravity calculated from X-ray intensities measured along the x-axis direction.
Figure 5:
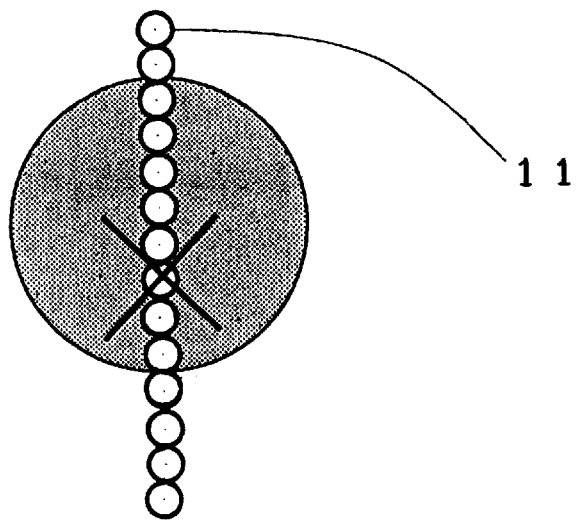
FIG. 5 is a diagram illustrating measurements performed by scanning in the y-axis direction.
Figure 6:
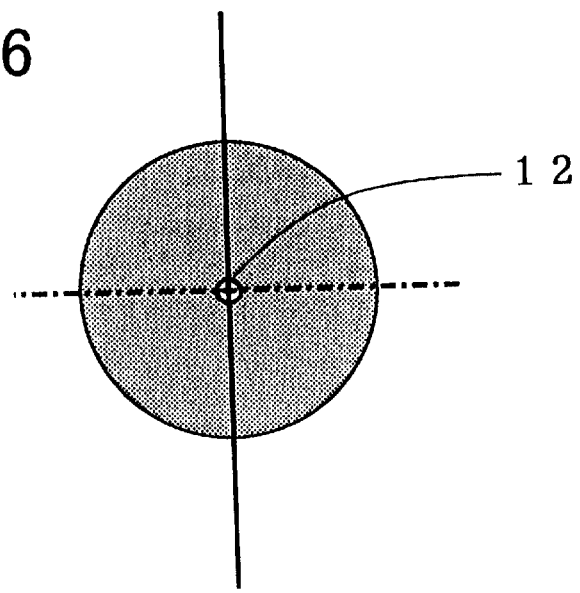
FIG. 6 is a diagram illustrating a process in which the y-coordinate of the center of the circular sample is determined based on a center of gravity calculated from X-ray intensities measured along the y-axis direction.
Figure 7:
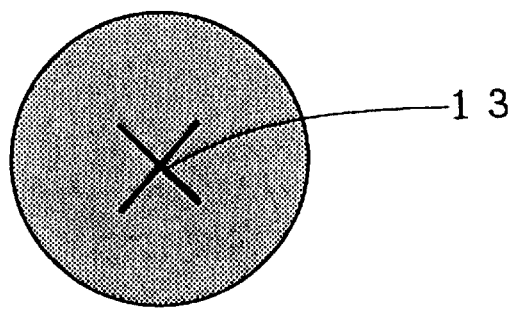
FIG. 7 is a diagram illustrating a condition where the center of the circular sample has been determined.
Figure 8:
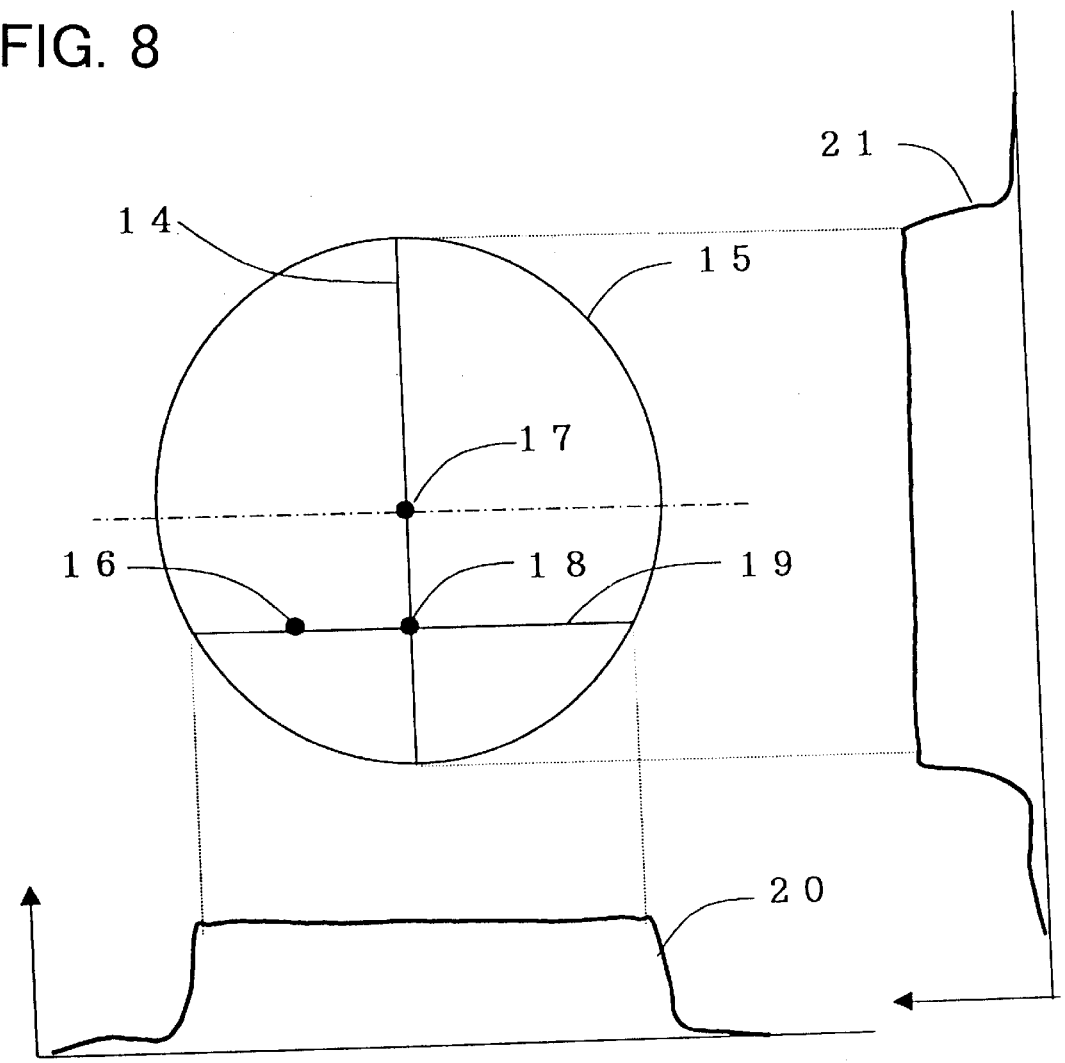
FIG. 8 is a diagram for explaining the operation of this invention.
Figure 9:
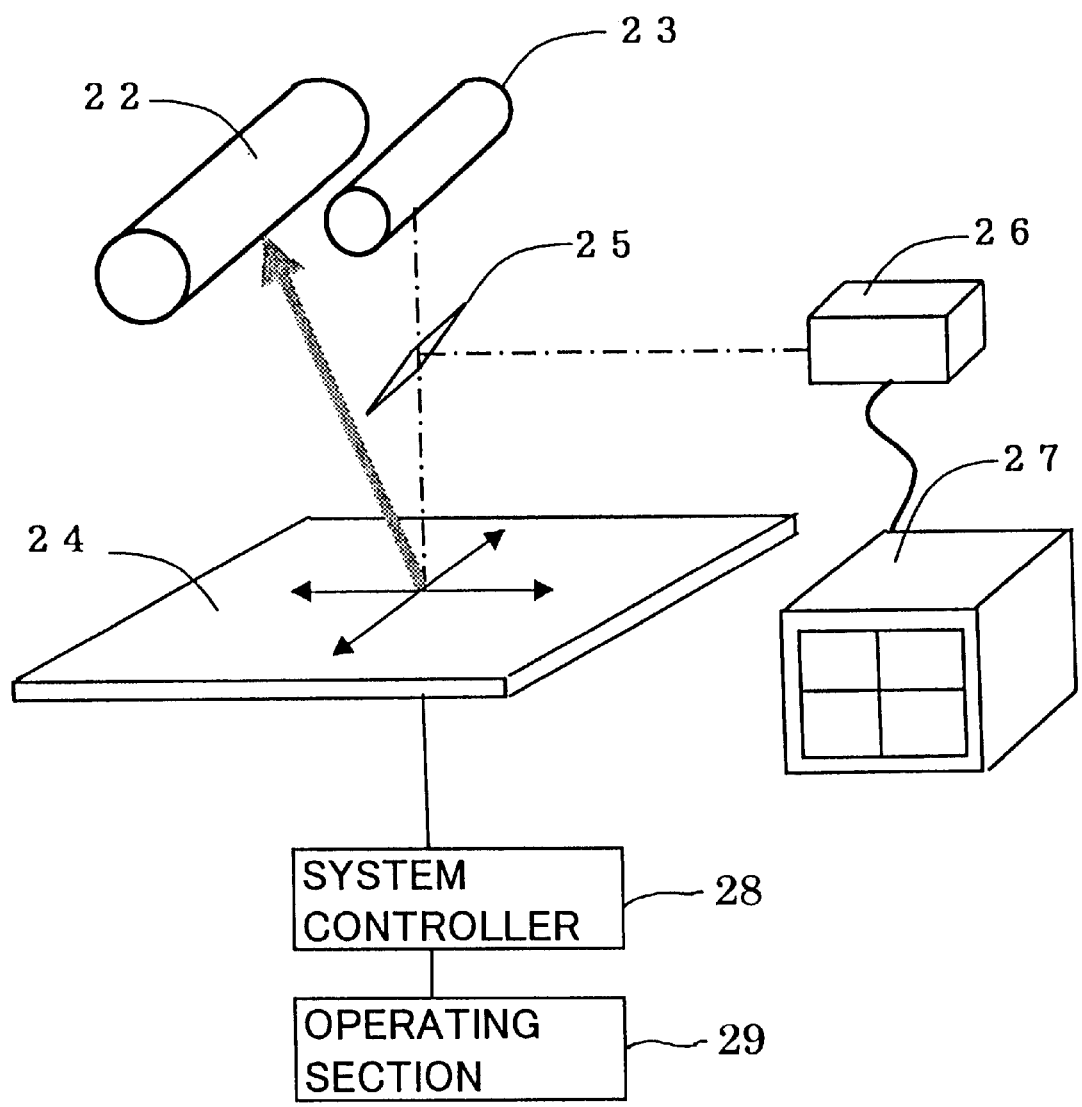
FIG. 9 is a diagram illustrating a conventional system configuration in which this invention can be performed.

FIG. 1 is a flowchart containing steps 1–6 of a procedure for determining the center of a circular sample in an X-ray fluorescence analyzer according to the present invention. Hereinafter is explained the flowchart referring to FIGS. 2–7, in which the center of a circular sample is determined. After loading a circular sample 8 on a sample table, the center of the circular sample is coarsely aligned with crisscross lines by using a sample observation monitor to determine provisional center coordinates 7(FIG. 2). The circular sample 8 is then measured by scanning it with an X-ray generated by an X-ray generator 23 (FIG. 9) in the direction of the x-axis using the coordinates of the provisional center 7 as a reference. This scanning operation is performed in the following conditions: the scanning range is set to twice the diameter of the circular sample; the interval between successive points of scanning is made equal to the width of each spot exposed to an X-ray beam as measured in the x-axis direction; and individual measuring points 9 are taken in the x-axis direction(FIG. 3) by a detector 22 (FIG. 9). In measurements in this scanning operation, the sample is exposed to X-ray radiation and the intensities of fluorescent X-rays reflected by the sample are obtained. while the time required for each measurement is dependent on the required positioning accuracy, practically sufficient information can be obtained with about one-second measurement time. A central x-coordinate 10 of the circular sample is determined based on a center of gravity calculated from x-coordinates of the individual measuring points and fluorescent X-ray intensities(FIG. 4). Subsequently, measurements by the scanning method are performed in the y-axis direction using the central x-coordinate and the y-coordinate of the provisional center as a reference. Conditions imposed on this scanning operation are as follows: the scanning range is set to twice the diameter of the circular sample; the interval between successive points of scanning is made equal to the width of each spot exposed to the X-ray beam as measured in the y-axis direction; and individual measuring points 11 are taken in the y-axis direction(FIG. 5). In measurements in this scanning operation, the sample is exposed to X-ray radiation and the intensities of fluorescent X-rays remitted from the sample are obtained in a manner similar to the measurements in the scanning operation in the x-axis direction. A central y-coordinate 12 of the circular sample is determined based on a center of gravity calculated from y-coordinates of the individual measuring points and fluorescent X-ray intensities(FIG. 6).

The sample table 24 is controlled by using the x-coordinate and the y-coordinate of the center 13(shown in FIG. 7) of circular sample obtained the aforementioned operations, and subsequent measurements for analysis are performed. Measurement time selected for analysis is different from that taken in determining the center of the sample.

Secondly, another embodiment is now described, in which the scanning range, the interval between successive scanning points and measurement time allocated for searching the center are varied in accordance with the required positioning accuracy.

It is not absolutely necessary to scan the circular sample over a distance equal to twice its diameter, because the scanning range is sufficient, by its nature, if it is just large enough to fully span the sample in its lateral and longitudinal directions. It is possible to set the time for searching the center of the sample to its minimum since the scanning range can be varied in accordance with the dimensions of the sample, the performance of an optical sample observation system and means for determining the provisional center of the sample. If the scanning range is decreased by 30%, the time for searching operation is also reduced by 30%, because the scanning range and necessary search time are proportional to each other.

The interval between successive scanning points is determined, by its nature, in accordance with the dimensions of the X-ray beam spot, the dimensions of the sample and the accuracy required for determining the center of the sample. The dimensions of the sample are usually significantly larger than those of the X-ray beam spot and essential requirements are that the sample be hit by the X-ray beam in a reliable manner for determining the center of the sample in most cases. The interval between successive scanning points may be made larger than the width of the X-ray beam in such cases, enabling a reduction in the time required for searching. On the contrary, when the dimensions of the sample are almost equal to those of the X-ray beam spot, the X-ray beam can be aligned with the sample by moving the sample at finely spaced intervals.

Since the measurement time is sufficient if it is long enough to permit identification of the boundary of the sample, the time required for each measurement is determined by the extent of changes in fluorescent X-ray intensities between a location where the sample is absent and a location where the sample exists. When determining the center of an extremely thin sample, however, the measurement time is set to about 10 seconds so that extremely small intensity variations can be detected.

Figure 10:
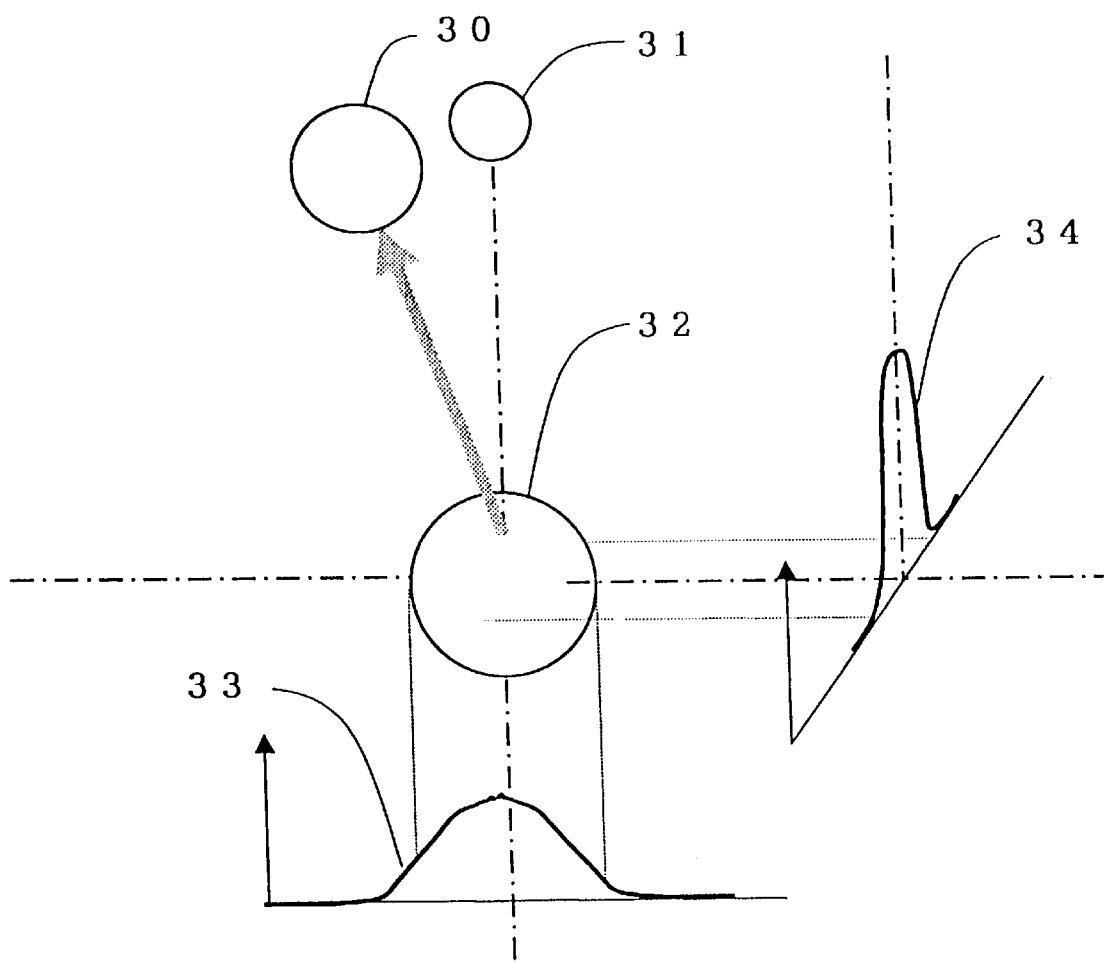
FIG. 10 shows fluorescent X-ray intensity distributions obtained when determining the center of a spherical sample.

Thirdly, the invention is described with reference to a case of another embodiment, in which an object whose center should be determined is a sample having the shape of a sphere. Distribution of fluorescent X-ray intensities radiated from a spherical sample can achieve point symmetry around the origin of an xy coordinate system established on the center of the sphere by disposing an X-ray generator 31 and an X-ray detector 30 at an angle of elevation close to 90 degrees with respect to an xy-plane. For this reason, the aforementioned method of the invention, in which the center of gravity is regarded as the center of a sample, is applicable as a method for determining the center of the spherical sample 32. More particularly, the center of gravity of a fluorescent X-ray intensity distribution 33 obtained from measurements by scanning in the x-axis direction of FIG. 10 and that of a fluorescent X-ray intensity distribution 34 obtained from measurements by scanning in the y-axis direction approximately coincide with the center coordinates of the sphere. Since an X-ray detector 30 of FIG. 10 is placed to the left of an X-ray generator 31, where the angle of incidence of fluorescent X-rays is 70 degrees with respect to the xy-plane, a small deviation occurs between the x-coordinate of the center of the sphere and the determined x-coordinate. However, the amount of this deviation is so small that its effect on analysis operation is almost negligible. Especially when utilizing the invention for quality control purposes, for instance, such a small positional deviation does not cause any problem because great importance is placed on reproducibility of analysis of the same point.

Another embodiment is now described, in which an object whose center should be determined is an elliptical or a rectangular sample which is bilaterally symmetrical about the x-axis and y-axis. In the case of a rectangular sample, for example, it is possible to obtain the same data as a fluorescent X-ray intensity distribution 20 in the x-axis direction and a fluorescent X-ray intensity distribution 21 in the y-axis direction obtained with a circular sample 15 and thereby calculate center coordinates, or the center of gravity of the sample, if the sample is placed so that one side of its rectangular shape lies exactly on the x-axis.

This invention makes it possible to determine the center of a sample having a circular, elliptical or rectangular shape, for instance, which is bilaterally symmetrical about the x-axis and y-axis. As electronic components, one of product categories to be analyzed, are increasingly miniaturized in recent years, their positioning in X-ray analysis has become an important consideration. Factors to be considered are: firstly, sample positioning accuracy and its reproducibility; secondly, time required for positioning operation; and thirdly, automation.

Concerning the first factor, or positioning accuracy and its reproducibility, the present invention makes it possible to determine an exact sample position even when there exists a positional deviation between a sample observation system employing a camera and a spot actually exposed to X-ray radiation, because the location of the sample is determined by actually emitting the X-ray radiation. In regard to the reproducibility, it is possible to consistently determine specified positions without any human error, because the sample position is determined by using a procedure which would render human operation completely unnecessary or position determination not dependent on human operation. The capability of ensuring good reproducibility is considerably important in analyzing operation. With this invention, such analyzing. errors that X-rays are projected on an area where no sample is placed become least likely to occur.

Concerning the second f actor, or time required for positioning operation, the invention makes it possible to determine the center of a sample in a significantly shorter time compared to determining the position by lattice pattern scanning and, then, adjust the scanning range, the interval between successive scanning points and measurement time allocated for positioning, enabling further time savings.

Concerning the third factor, or automation, the invention enables automation of analysis if information on sample dimensions and approximate position where the sample should be placed. As an example, if a jig for sample measurement is prepared and information on coordinates of a position where the sample is placed is stored in memory, a procedure for determining a provisional center is automated, thereby enabling automatic measurement of a plurality of samples.

What is claimed is:
1. In an X-ray fluorescence analyzer comprising a controllable sample table which can control at least the x-coordinate and the y-coordinate of a sample in an xy-plane, a sample monitor which enables verification of a spot exposed to X-ray radiation, an X-ray generator, an X-ray detector, an operating section for inputting and displaying information, and a system controller for performing overall system control, a method for determining the center of a circular sample which is placed on the sample table comprising the steps of:

using the sample monitor to determine a provisional center of the sample and coarsely aligning the sample center with the X-ray generator;

scanning the circular sample over a scanning range in the x-axis direction with an X-ray beam and measuring fluorescent X-ray intensities of individual points using the provisional center as a reference point wherein the scanning range in the x-axis direction is set to twice the diameter of the circular sample and the interval between successive scanning points is made equal to the width of each spot exposed to the X-ray beam as measured in the x-axis direction;

determining the central x-coordinate of the sample by calculating a center of gravity of the fluorescent X-ray intensities in the x-axis direction based on the measured fluorescent X-ray intensities and x-coordinates obtained from the measurements in the x-axis direction;

scanning the circular sample over a scanning range in the y-axis direction with the X-ray beam using the central x-coordinate of the sample and the y-coordinate of the provisional center as a reference, wherein the scanning range in the y-axis direction is set to twice the diameter of the circular sample and the interval between successive scanning points is made equal to the width of each spot exposed to the X-ray beam as measured in the x-axis direction and measuring fluorescent X-ray intensities of individual points; and determining the central y-coordinate of the sample by calculating a center of gravity of the fluorescent X-ray intensities in the y-axis direction based on the measured fluorescent X-ray intensities and y-coordinates obtained from the measurements in the y-axis direction.

2. A method according to claim 1; wherein the scanning ranges in the x-axis and y-axis directions, the interval between successive scanning points in the x-axis and y-axis directions and measurement time allocated for performing the scanning in the x-axis and y-axis directions to determine the center of the sample are varied to achieve a desired positioning accuracy.

3. A method according to claim 1; wherein the sample is a spherical sample and is treated as a circular sample by disposing the X-ray generator and the X-ray detector at an angle of elevation close to 90 degrees with respect to the xy-plane.

4. A method according to claim 2; wherein the sample is a spherical sample and is treated as a circular sample by disposing the X-ray generator and the X-ray detector at an angle of elevation close to 90 degrees with respect to the xy-plane.

5. A method according to claim 1; wherein the sample is an elliptical or a rectangular sample placed in the xy-plane and which is bilaterally symmetrical about the x-axis and y-axis.

6. A method according to claim 2; wherein the sample is an elliptical or a rectangular sample placed in the xy-plane and which is bilaterally symmetrical about the x-axis and y-axis.

* * * * *